(12) United States Patent
Lafont et al.

(10) Patent No.: US 11,229,670 B2
(45) Date of Patent: Jan. 25, 2022

(54) COMPOSITIONS USEFUL FOR THE TREATMENT OF IMMUNE-RELATED DISEASES

(71) Applicant: SCARCELL THERAPEUTICS, Paris (FR)

(72) Inventors: Antoine Lafont, Paris (FR); Bernard Coulomb, Igny (FR)

(73) Assignee: SCARCELL THERAPEUTICS, Paris (FR)

(*) Notice: Subject to any disclaimer, the term of this patent is extended or adjusted under 35 U.S.C. 154(b) by 182 days.

(21) Appl. No.: 16/461,834

(22) PCT Filed: Nov. 18, 2017

(86) PCT No.: PCT/EP2017/079698
§ 371 (c)(1),
(2) Date: May 17, 2019

(87) PCT Pub. No.: WO2018/091698
PCT Pub. Date: May 24, 2018

(65) Prior Publication Data
US 2019/0269736 A1 Sep. 5, 2019

(30) Foreign Application Priority Data
Nov. 18, 2016 (EP) .................................... 16306514

(51) Int. Cl.
A61K 35/33 (2015.01)
A61P 17/06 (2006.01)
A61K 8/98 (2006.01)
A61K 9/00 (2006.01)
A61K 31/56 (2006.01)
A61K 35/36 (2015.01)
A61K 45/06 (2006.01)
(Continued)

(52) U.S. Cl.
CPC .............. A61K 35/33 (2013.01); A61K 8/981 (2013.01); A61K 9/0014 (2013.01); A61K 31/56 (2013.01); A61K 35/36 (2013.01); A61K 45/06 (2013.01); A61P 17/06 (2018.01); A61P 37/00 (2018.01); A61Q 19/007 (2013.01)

(58) Field of Classification Search
CPC ..................................................... A61K 35/33
See application file for complete search history.

(56) References Cited

U.S. PATENT DOCUMENTS

2016/0151274 A1  6/2016  Lafont et al.
2016/0256496 A1  9/2016  Gogly et al.

FOREIGN PATENT DOCUMENTS

WO  2007001016 A1  1/2007
WO  2008017927 A2  2/2008
WO  2009121761 A1  10/2009
(Continued)

OTHER PUBLICATIONS

English Abstract of KR120045562B B1 Mar. 21, 2013, "Invitrogen medium useful for culturing animal cell used in skin conditioning composition used for e.g. treating inflammatory skin disease, comprises animal blood serum component, stigmasterol and N-acetylgalactosamine".

Primary Examiner — Rosanne Kosson
(74) Attorney, Agent, or Firm — Browdy and Neimark, PLLC

(57) ABSTRACT

The present invention relates to a gingival fibroblast-derived product for use in the treatment or prevention of an immune-related disease in an individual.

9 Claims, 4 Drawing Sheets

(51) Int. Cl.
*A61Q 19/00* (2006.01)
*A61P 37/00* (2006.01)

(56) References Cited

FOREIGN PATENT DOCUMENTS

| WO | 2011070305 A1 | 6/2011 |
| WO | 2012121695 A1 | 9/2012 |
| WO | 2015004216 A1 | 1/2015 |

COMPOSITIONS USEFUL FOR THE TREATMENT OF IMMUNE-RELATED DISEASES

FIELD OF THE INVENTION

The present invention relates to compounds and compositions useful for the treatment of immune-related diseases, in particular for the treatment of atopic dermatitis, in an individual.

BACKGROUND OF THE INVENTION

Immune-related diseases represent an important part of debilitating diseases in humans. Indeed, these diseases notably encompass autoimmune diseases, inflammatory diseases, in particular inflammatory skin diseases, and allergic diseases, including dermatitis, atopic dermatitis, inflammatory skin rash, asthma and arthritis.

Although the aetiology of these conditions is unknown for the most part, immune-related diseases result from a dysregulation of the normal immune response. This immune dysregulation often involves the inappropriate activation of inflammatory cytokines, such as TSLP (Thymic stromal lymphopoietin) (Cianferoni et al. (2014) *Expert Rev. Clin. Immunol.* 10: 1463-1474) and CCL26 (Kagami et al. (2005) *Clinical and Experimental Immunology* 141:459-466; Sera et al. (2008) *An. Bras. Dermatol.* 83:57-73).

By way of example, atopic dermatitis, also known as eczema, is a multifactorial disease associated to an alteration of the epidermal barrier and a high sensitivity to allergens. It generally evolves by recurrent inflammatory flare-ups. The major symptoms of atopic dermatitis are skin dryness (xerosis), erythema, itching, and red plates. It generally starts in childhood and it is considered that 15 to 20% of infants suffer from atopic dermatitis in developed countries. The further development of this disease often leads to asthma in adolescents and allergic rhinitis in adults. In addition, the disease often leads to significant physical and psychological distress.

The usual pharmaceutical treatment of inflammatory skin diseases, such as atopic dermatitis, involves topical steroids, in particular dexamethasone (Hon et al. (2015), *Hong Kong Med. J.,* 21: 251-261.), which are used to reduce inflammation. In complement to topical steroids, daily care, e.g. soap-free cleansing lotions and moisturizers, is essential in particular for decreasing skin dryness. However, steroid-based treatments have several side effects, such as skin atrophy, and their effectivity decreases over time. In addition, they are generally poorly tolerated by the patients. More generally, treatments currently available for atopic dermatitis are exclusively symptomatic and are unable to maintain a long-lasting remission.

Accordingly, there is a need for an alternative to these therapies, which would be effective to cure immune-related diseases in addition to treating the symptoms.

SUMMARY OF THE INVENTION

The present invention arises from the unexpected finding by the inventors that gingival fibroblast-conditioned medium can inhibit the secretion of inflammatory cytokines TSLP, CCL-26 and IL-1β by human keratinocytes (i.e. skin cells) submitted to inflammatory conditions.

Thus, the present invention relates to a gingival fibroblast-derived product for use in the treatment or prevention of an immune-related disease in an individual.

In an embodiment of the invention, the above-defined gingival fibroblast-derived product is associated with at least one agent intended for the prevention or treatment of inflammatory skin disease, in particular selected from the group consisting of a corticosteroid, a calcineurin inhibitor, an emollient and a moisturizer.

The invention also relates to a composition comprising a gingival fibroblast-derived product for use in the prevention or treatment of an immune related disease.

The invention also relates to a composition comprising a gingival fibroblast-derived product as defined above and further comprising at least one agent intended for the prevention or treatment of inflammatory skin disease and optionally comprising at least one pharmaceutically acceptable carrier or excipient, in particular for use in the prevention or treatment of an immune related disease.

The invention also relates to the non-therapeutic use of a gingival fibroblast-derived product for the cosmetic treatment of skin dryness of an individual, optionally associated with at least one cosmetic agent intended for the cosmetic treatment of skin dryness.

The invention also relates to a cosmetic composition comprising a gingival fibroblast-derived product and at least one cosmetic agent intended for the cosmetic treatment of skin dryness, and optionally at least one cosmetically acceptable carrier or excipient.

The invention also relates to a method for preventing or treating an inflammatory skin disease in an individual, comprising administering to the individual a prophylactically or therapeutically effective amount of a gingival fibroblast-derived product.

The invention also relates to the above-defined method for preventing or treating an inflammatory skin disease further comprising administering to the individual at least one agent intended for the prevention or treatment of inflammatory skin disease, preferably selected from the group consisting of a corticosteroid, a calcineurin inhibitor, an emollient and a moisturizer.

The invention also relates to a method for the cosmetic treatment of skin dryness in an individual, comprising administering to the individual a cosmetically effective amount of a gingival fibroblast-derived product and optionally at least one cosmetic agent intended for the cosmetic treatment of skin dryness.

The invention also relates to a method for the cosmetic treatment of skin dryness in an individual, comprising administering to the individual a cosmetic composition comprising a gingival fibroblast-derived product and further comprising at least one cosmetic agent intended for the cosmetic treatment of skin dryness, and optionally at least one cosmetically acceptable carrier or excipient.

DETAILED DESCRIPTION OF THE INVENTION

As intended herein, the term "comprising" has the meaning of "including" or "containing", which means that when an object "comprises" one or several elements, other elements than those mentioned may also be included in the object. In contrast, when an object is said to "consist of" one or several elements, the object is limited to the listed elements and cannot include other elements than those mentioned.

Immune-Related Disease

As intended herein, an "immune-related disease" refers to any disease which is linked or due to a dysfunction, in particular a dysregulation, such as an over-activation of the immune system.

The immune-related disease according the invention is preferably selected from the group consisting of an inflammatory disease, in particular a chronic inflammatory disease, an inflammatory skin disease, an auto-immune disease and an allergic disease. More preferably, the immune-related disease according to the invention is selected from the group consisting of an inflammatory skin disease, iritis and asthma.

Preferably, the inflammatory skin disease according to the invention is a chronic inflammatory skin disease. Preferably also the inflammatory skin disease according to the invention is selected from the group consisting of dermatitis, inflammatory skin rash, ichthyosis and psoriasis.

Preferably, the immune-related disease is dermatitis. Dermatitis refers to a group of pruritic chronic inflammatory skin diseases well known to the one of ordinary skill in the art and which are notably defined in classes L20 to L30 in the 10th revision of the International Classification of Diseases (ICD-10) 2016 version by the World Health Organization.

Dermatitis according to the invention is thus preferably selected form the group consisting of:
Atopic dermatitis (e.g. L20 ICD-10),
Seborrhoeic dermatitis (e.g. L21 ICD-10),
Diaper dermatitis (e.g. L22 ICD-10),
Allergic contact dermatitis (e.g. L23 ICD-10),
Irritant contact dermatitis (e.g. L24 ICD-10),
Unspecified contact dermatitis (e.g. L25 ICD-10),
Exfoliative dermatitis (e.g. L26 ICD-10),
Dermatitis due to substances taken internally (e.g. L27 ICD-10),
Lichen simplex chronicus and prurigo (e.g. L28 ICD-10), and
Pruritus (e.g. L29 ICD-10).

More preferably, the immune-related disease according to the invention is atopic dermatitis. As intended herein dermatitis is also named eczema.

The chronic inflammatory disease according to the invention is preferably selected from the group consisting of rheumatoid arthritis, lupus erythematosus and multiple sclerosis.

Inflammatory skin rash according to the invention is notably defined in class R21 of ICD-10. Ichthyosis according to the invention is notably defined in classes L85 and Q80 of ICD-10. Psoriasis according to the invention is notably defined in class L40 of ICD-10. Lupus erythematosus according to the invention is notably defined is class L93 of ICD-10. Asthma according to the invention is notably defined is class J45 of ICD-10. rheumatoid arthritis according to the invention is notably defined in class M06 of ICD-10. Iritis according to the invention is notably defined in class H19 of ICD-10. Multiple sclerosis according to the invention is notably defined in class G35 of ICD-10.

Individual

As intended herein, the "individual" according to the invention is preferably a mammal, more preferably a human, or a pet animal. Most preferably, the individual according to the invention is a human.

Preferably, the individual according to the invention is an infant, a child or an adolescent. Preferably also, the individual according to the invention is a human adult.

In an aspect of the invention, the individual according to the invention can have one or more symptoms of an immune-related disease.

In another aspect of the invention, the individual according to the invention does not suffer from an immune-related disease, in particular an inflammatory skin disease according of the invention. This may notably be the case in the frame of the non-therapeutic use or of the cosmetic treatment of skin dryness according to the invention.

Gingival Fibroblast-Derived Product

As intended herein, "gingival fibroblast-derived product" relates to any product which can be obtained from gingival fibroblasts in themselves or which contains gingival fibroblasts secretions. The gingival fibroblast-derived product according to the invention is preferably selected form the group consisting of gingival fibroblast whole cells, a gingival fibroblast culture, a gingival fibroblast extract, and a gingival fibroblast conditioned medium.

Procedures for taking, culturing and preserving gingival fibroblasts are well known to one of ordinary skill in the art and are particularly described in Naveau et al. (2006) *J. Periodontol.* 77:238-47 and in Gogly et al. (2007) *Arterioscler. Thromb. Vasc. Biol.* 27:1984-90. Preferably, gingival fibroblasts are sampled and cultured in a serum-free medium in presence of platelet lysate as described in Doucet et al. (2005) *J Cell Physiol.* 205:228-36. In particular, gingival fibroblasts can be obtained by culturing a gingival sample or biopsy, optionally after enzymatic digestion of the sample or the biopsy to free gingival fibroblasts therefrom. As such, the cells originating from the culture of a gingival sample or biopsy are essentially gingival fibroblasts.

The gingival fibroblast extract can be obtained by any cell fragmentation method known in the art. Preferably the gingival fibroblast extract according to the invention is selected from the group consisting of a membrane extract, a cytoplasmic extract or a nuclear extract.

Preferably, the gingival fibroblast conditioned medium according to the invention relates to a liquid cell-culture medium, in particular a serum-free culture medium and/or a culture medium comprising platelet lysate, which has been contacted by gingival fibroblasts, in particular for a time sufficient for the gingival fibroblasts to have secreted in the medium. Thus, the gingival fibroblast conditioned medium according to the invention contains gingival fibroblast secretions.

It is well within the common skills of one of ordinary skill in the art to determine which culture medium is suitable for gingival fibroblast in it. In particular, the culture can be of any type known to one of ordinary skill in the art to sustain survival and/or growth of gingival fibroblasts. By way of example of suitable gingival fibroblast conditioned medium according to the invention stand Dulbecco's Modified Eagle's Medium (DMEM), Eagle's Minimum Essential Medium (MEM or EMEM), Eagle's Minimum Essential Medium Alpha Modification (Alpha MEM) and Basal Medium Eagle (BME).

Preferably, the gingival fibroblasts have been in contact with the culture medium for at least 2, 4, 6, 8, 10, 12, 24, 36 or 48 hours. Preferably also, the gingival fibroblasts have been in contact with the culture medium for less than 72, 56 or 48 hours.

The gingival fibroblast conditioned medium according to the invention can be subjected to treatment steps such as centrifugation, filtration, or concentration. In particular, the gingival fibroblast conditioned medium according to the invention can be a concentrated gingival fibroblast conditioned medium, more particularly a gingival fibroblast conditioned medium concentrated 2, 5, 10, 25 or 50 times with respect to the unconcentrated gingival fibroblast conditioned medium from which it derives.

Preferably, the gingival fibroblast-derived product for use according to the invention comprises:
taking the gingival fibroblasts from the individual;
culturing the gingival fibroblasts;
obtaining a gingival fibroblast-derived product from the cultured gingival fibroblasts;
administering the gingival fibroblast-derived product to the individual.

Preferably, gingival fibroblasts according to the invention are autologous, which means they are taken from the individual to whom the gingival fibroblast-derived product is intended to be administered. However, the gingival fibroblasts according to the invention can also be allogenic, which means they are taken from another individual of the same species, or heterologous, which means they are taken from another individual of another species.

Administration

Preferably, the gingival fibroblast-derived product according to the invention is administered in a prophylactically or therapeutically effective amount for preventing or treating an inflammatory skin disease. Preferably also, the gingival fibroblast-derived product according to the invention is administered in a cosmetically effective amount for treating skin dryness.

The administration of the gingival fibroblast-derived product or the pharmaceutical or cosmetic composition comprising the gingival fibroblast-derived product according to the invention can proceed by any method known in the art. Preferably, the administration of the gingival fibroblast-derived product or the pharmaceutical or cosmetic composition comprising the gingival fibroblast-derived product is at a site near or on the skin area to be treated. More preferably, the gingival fibroblast-derived product or the pharmaceutical or cosmetic composition comprising the gingival fibroblast-derived product is administered subcutaneously, intravenously, intramuscularly, intra-dermally or topically, near or on the skin area to be treated. Most preferably, the gingival fibroblast-derived or the pharmaceutical or cosmetic composition comprising the gingival fibroblast derived-product is administered topically.

Preferably, the skin area to be treated according to the invention refers to a site where one or more symptoms of the inflammatory skin disease according to the invention are visible or in close proximity of this site. Preferably also, the skin area to be treated according to the invention refers to a site where one or more effects of skin dryness according to the invention are visible or in close proximity of this site.

Preferably, the gingival fibroblast-derived product or the pharmaceutical or cosmetic composition comprising the gingival fibroblast-derived product is under the form of a lotions, a cream, an ointment, a gel, a sprays a wipe, a pad or a patch.

Additional Compounds

The agent for the prevention or treatment of the inflammatory skin disease according to the invention, in particular atopic dermatitis, can be of any type known to one of ordinary skill in the art. Preferably, the agent for the prevention or treatment of atopic dermatitis and/or inflammatory skin rashes according to the invention is selected from the group consisting of a corticosteroid, a calcineurin inhibitor, an emollient, and a moisturizer.

The corticosteroid according to the invention can be of any type well known to one of ordinary skill in the art such as dexamethasone, betamethasone, prednisolone, prednisone, tixocortol and triamcinolone.

The calcineurin inhibitor can be of any type well known to one of ordinary skill in the art such as cyclosporine and cyclosporine modified.

The emollient according to the invention can be of any type well known to one of ordinary skill in the art such as paraffin, silicon, dimethicon, arachydyl alcohol, cetyl stearyl, cearyl alcohol, palm glycerides, mineral oil, petrolatum, oleic acid, ethyl linoleate, glyceride derivatives, lanoline and glycerol.

The moisturizer according to the invention can be of any type well known to one of ordinary skill in the art such as a cream, an ointment and a lotion.

Pharmaceutical Composition

As intended herein, "pharmaceutically acceptable carrier or excipient" refers to any material suitable with a pharmaceutical composition. Preferably, the pharmaceutically acceptable carrier or excipient according to the invention is suitable for a topical administration.

Preferably, the pharmaceutically acceptable carrier or excipient according to the invention, includes but is not limited to any of the standard carrier or excipient known to one of ordinary skill in the art such as water, glycerine, alcohol, oil emulsion, water emulsion, buffered saline solution, preservative, stabilizer and wetting agents.

Non-Therapeutic Use

As intended herein, "skin dryness" according to the invention refers to a non-pathological dry skin. Skin dryness according to the invention is preferably associated with a red patch, a dry patch, visible dry lines, a discoloration of the skin, scabs, superficial burns, a feeling of skin tightness a skin irritation.

The cosmetic agent intended for the cosmetic treatment of skin dryness according to the invention can be of any type known to one of ordinary skill in the art. The cosmetic agent intended for the cosmetic treatment of skin dryness according to the invention is preferably selected from the group consisting of a moisturizer, an emollient, a hypoallergenic emollient, an ointment, soap-free products, a dermatological gel and a dermatological bar.

As intended herein, "cosmetically acceptable carrier or excipient" refers to any material which is suitable with a cosmetic composition. Preferably, the cosmetically acceptable carrier or excipient is suitable for a topical administration.

The cosmetically acceptable carrier or excipient according to the invention include but is not limited to any of the standard cosmetic carrier or excipient known to one of ordinary skill in the art such as water, vegetal oil, mineral oil, fatty acid alcohol and natural waxes.

The invention will be further described by the following non-limiting figures and Example.

EXAMPLE

A. Material and Methods

Figure 1A:
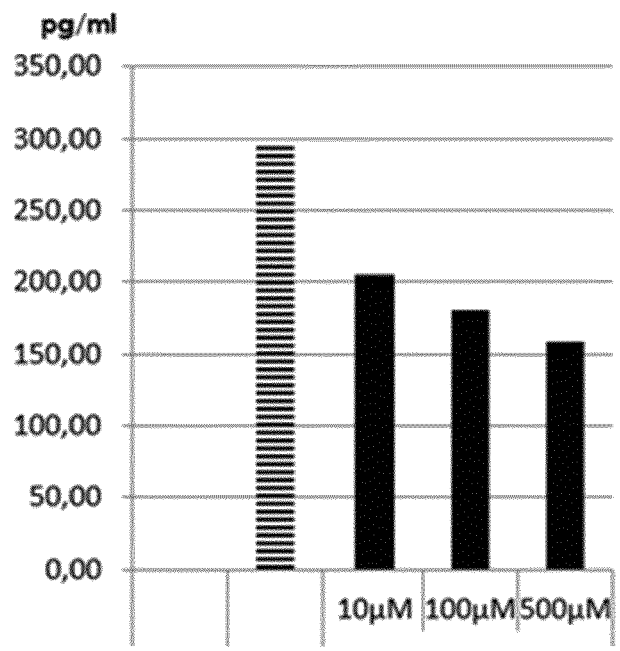
FIGS. 1A and 1B represent the level of secretion (vertical axis pg/ml) of CCL26 (FIG. 1A) and TSLP (FIG. 1B) by keratinocytes in a simultaneous treatment. The experiment was conducted in low inflammatory condition. Dexamethasone (black bars) has been tested at 10 µM, 100 µM and 500 µM compared to the control (hatched bar).

1. Human Gingival Fibroblasts 1.1. Culture Cell

Human gingival fibroblasts (GF) were obtained from healthy donors. After enzymatic dissociation of gingival biopsies (collagenase, dispase), gingival fibroblasts were cultured in a serum-free medium in presence of platelet lysate (Doucet et al. (2005) *J Cell Physiol.* 205:228-36).

1.2. Preparation of Gingival Fibroblast Conditioned Medium

The culture medium of confluent GF was discarded. After rinsing (PBS), fresh medium was added (without platelet lysate and without antibiotics). Cells were incubated at 37° C. for 24 hours. The conditioned medium (CM) was collected, aliquoted and stored at −80° C. These steps can be performed with different passage cells.

1.3 Concentration of CM

The media were centrifuged on a concentration membrane (Millipore, Amicon 3K) and then stored at −80° C.

2. Human Keratinocytes

Keratinocytes were obtained from breast reconstruction of healthy donors. For expansion, cells were seeded into irradiated feeders in a suitable medium.

3. Protocol 3.1. Induction of Inflammation

A same combination of pro-inflammatory agents (IL-4, IL-13, TNFα, polyinosinic:polycytidylic acid (polyI:C) was used at 2 different concentrations:
  Low concentration: IL-4 10 ng/ml, IL-13 10 ng/ml, TNFα 5 ng/ml, polyI:C 5 µg/ml;
  High concentration: IL-4 100 ng/ml, IL-13 100 ng/ml, TNFα 20 ng/ml, polyI:C 10 µg/ml.

3.2. Anti-Inflammatory Treatment 3.2.1. Reference Products

Dexamethasone (from 100 µM to 500 µM) (Sigma Aldrich)

3.2.2. Gingival Fibroblast Conditioned Medium

The gingival fibroblast conditioned medium was concentrated for use at a final concentration from 5× to 50×. Three batches of conditioned media from various gingival fibroblasts donors have been used (GF009, GF010 and GF015)

3.3. Optimising the Time of Treatment

For the efficacy tests of CM, keratinocytes were seeded without feeder in 6-well plates with a medium suitable for cell culture without feeder (KSFM medium, Gibco).

4. Test Procedure 4.1. Simultaneous Treatment for the Induction of Inflammation

When the keratinocyte culture reached confluence, the culture medium of keratinocytes was replaced by a medium containing the pro-inflammatory agents (day 0) and the anti-inflammatory treatment (reference product or gingival fibroblast conditioned medium). The medium was collected on day 1 and stored at −80° C. until analysis.

4.2. Deferred Treatment for the Induction of Inflammation

When the keratinocyte culture reached confluence, the culture medium of keratinocytes was replaced by a medium containing pro-inflammatory agents (day 0). On day 1, the gingival fibroblast conditioned medium was directly added in the medium containing pro-inflammatory cytokines. The medium was collected on day 2 or day 5 and stored at −80° C. until analysis.

4.3. Analysis

The inflammatory condition of keratinocytes was determined by measuring inflammatory cytokine levels in their culture media. The studied cytokines were CCL26, TSLP and IL-1β. These cytokines were quantified with an ELISA assay (Duoset kit, R&D system).

B. Results

The present Example is based on an in vitro model of atopic dermatitis comprising:
  (i) growing keratinocytes until they reach confluence,
  (ii) stimulating them using a cocktail of pro-inflammatory agents, including PolyI:C, tumour necrosis factor (TNF-α), IL-4 and IL-13, known to be involved in atopic dermatitis inducement (Castex-Rizzi et al. (2014) *British Journal of Dermatology* 170 (suppl. S1):12-18; Le et al. (2009) *Allergy* 64:1226-1235) and
  (iii) determining the level of inflammatory cytokines/chemokines (TSLP, CCL26 and IL-1β) known to be involved in the pathogenesis of atopic dermatitis (Castex-Rizzi et al. op. cit., Le et al. op. cit., Cianferoni et al. op. cit. Kagami et al. op. cit. Sera et al. op. cit.) in the presence or absence of gingival fibroblast (GF) conditioned medium.

1. Anti-Inflammatory Effect of Reference Products (Simultaneous Treatment)

Figure 1B:
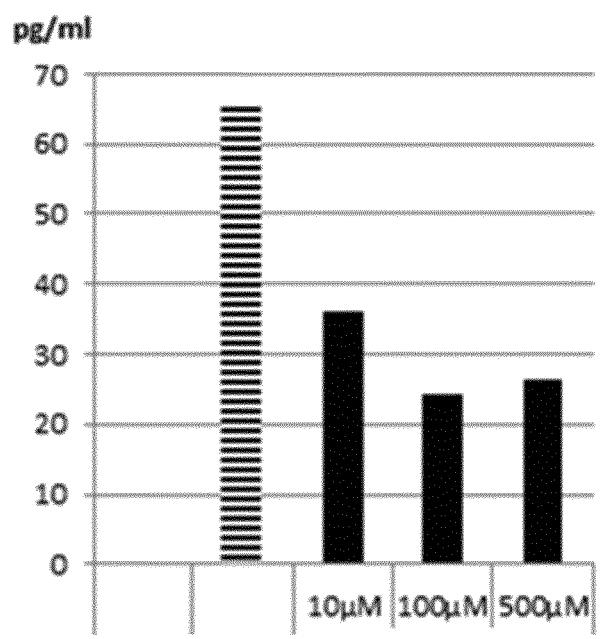

Results presented in FIGS. 1A-1B show that dexamethasone inhibits the secretion of CCL26 (FIG. 1A) and TSLP (FIG. 1B).

This model is thus relevant and dexamethasone can serve as reference product to evaluate the efficacy of gingival fibroblast conditioned medium to inhibit secretion of pro-inflammatory cytokines.

2. Anti-Inflammatory Effect of the Gingival Fibroblast Conditioned Medium (Simultaneous Treatment)

2.1. Induction of Inflammation with a Low Concentration of Inflammatory Agents

Figure 2:
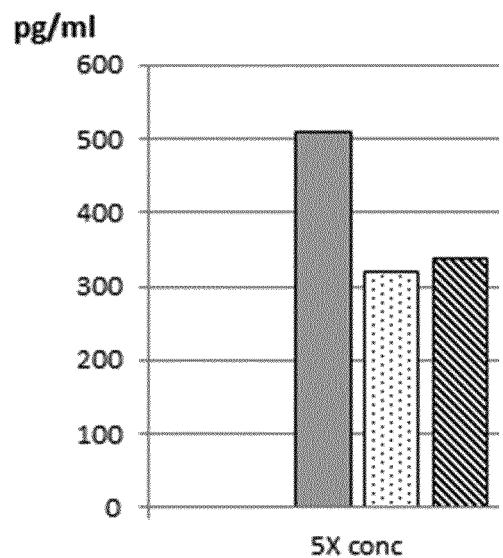
FIG. 2 represents the level of secretion (vertical axis pg/ml) of CCL26 by keratinocytes in a simultaneous treatment. The experiment was conducted in low inflammatory condition. Two batches of conditioned medium from various gingival fibroblasts donors have been used GF009 (dotted bar) and GF010 (hatched bar) compared to the control (grey bar). The two batches of conditioned medium have been tested at the concentration 5×.

Results presented in FIG. 2 show that the two tested batches of gingival fibroblast conditioned medium (GF009 and GF010) inhibit the secretion of CCL26 by inflammatory keratinocytes at the concentration 5×. Similar results were obtained for the secretion of TSLP and IL-1β.

2.2. Induction of Inflammation with a High Concentration of Inflammatory Agents

Figure 3A:
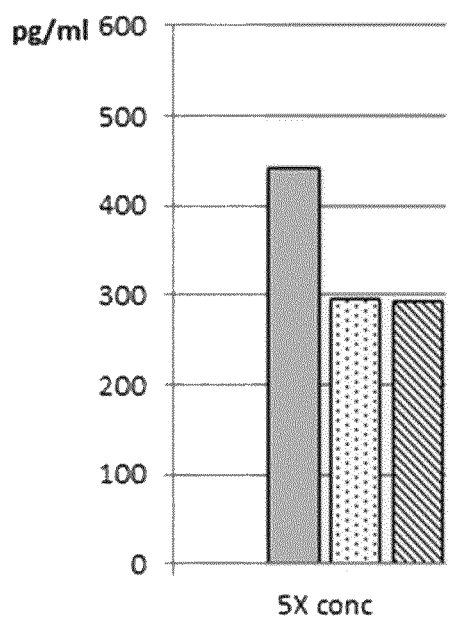
FIGS. 3A, 3B and 3C represent the level of secretion (vertical axis pg/ml) of CCL26 (FIG. 3A), TSLP (FIG. 3B) and IL-1β (FIG. 3C) by keratinocytes in a simultaneous treatment. The experiment was conducted in high inflammatory condition. Two batches of conditioned media from various gingival fibroblasts donors have been used GF009 (dotted bar) and GF010 (hatched bar) compared to the control (grey bar). The two batches of conditioned media have been tested at the concentration 5×.
Figure 3B:
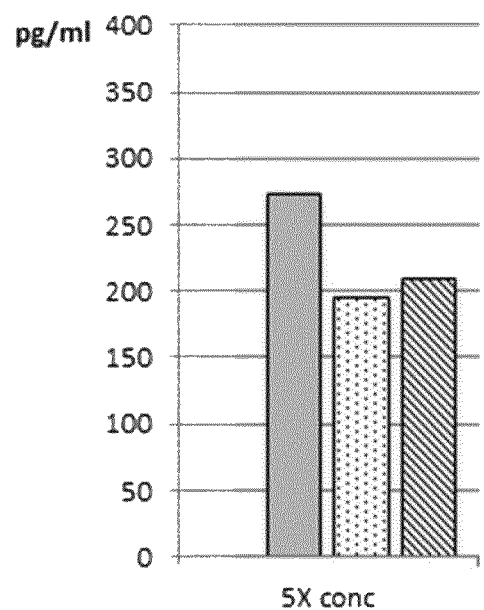
Figure 3C:
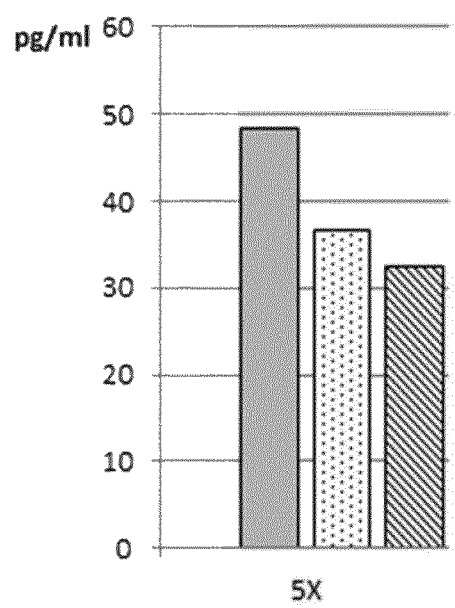

FIGS. 3A-3C show that gingival fibroblast conditioned medium inhibits the secretion of CCL26 (FIG. 3A), TSLP (FIG. 3B) and IL-1β (FIG. 3C)

2.3. Conclusion

Gingival fibroblast conditioned medium has an inhibitory effect on the secretion of inflammatory cytokines CCL26, TSLP and IL-1β by keratinocytes exposed to inflammatory conditions, even under highly inflammatory conditions.

3. Anti-Inflammatory Effect of the Gingival Fibroblast Conditioned Medium (Deferred Treatment)

3.1. Induction of Inflammation

Figure 4A:
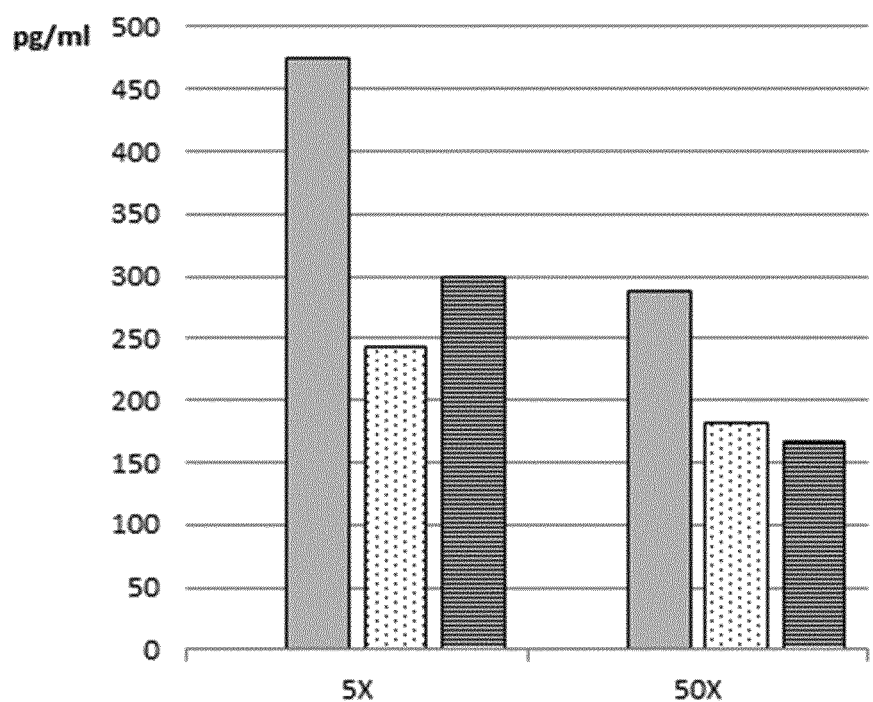
FIGS. 4A and 4B represent the level of secretion (vertical axis pg/ml) of CCL26 by keratinocytes in a deferred treatment. The experiment was conducted in low inflammatory condition. Two batches of conditioned media from various gingival fibroblasts donors have been used GF009 (dotted bar) and GF015 (hatched bar) compared to the control (grey bar). The two batches of conditioned media have been tested in two different concentrations: 5× and 50× and collected on day 2 (FIG. 4A) and day 5 (FIG. 4B).
Figure 4B:
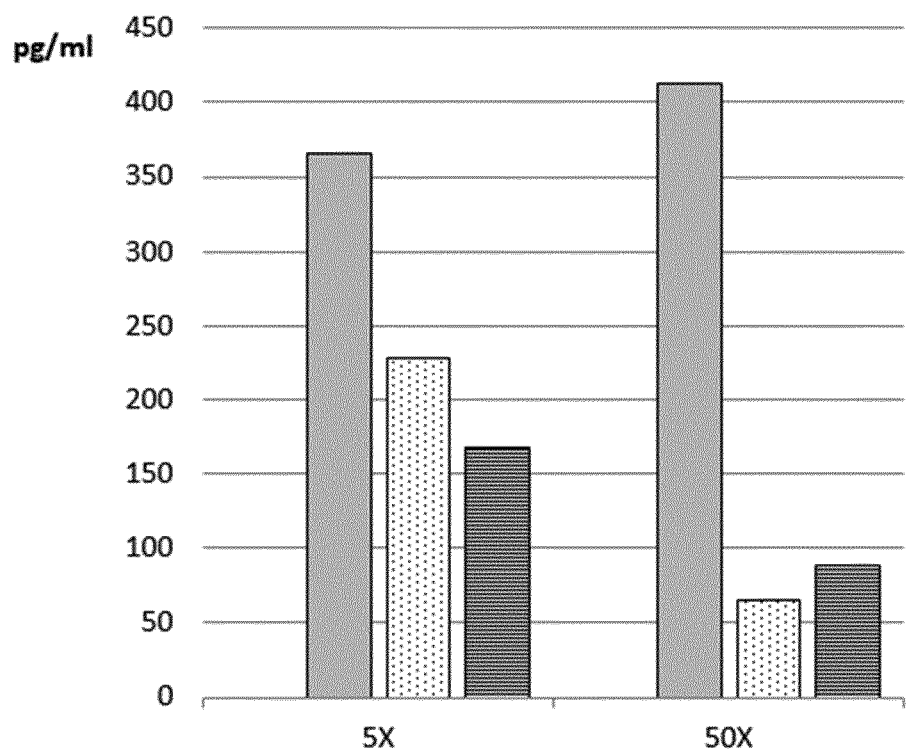

The two tested batches of gingival fibroblast conditioned medium (GF009 and GF010) inhibit the secretion of inflammatory cytokine CCL26 by inflammatory keratinocytes either at the concentrations 5× or 50× when collected on day 2 (FIG. 4A) and on day 5 (FIG. 4B).

3.2. Conclusion

Gingival fibroblast conditioned medium has a long term inhibitory effect on the secretion of inflammatory cytokines by keratinocytes exposed to inflammatory conditions, even when the inflammatory conditions are established for 24 hours before the keratinocytes are treated by the conditioned medium.

The invention claimed is:

1. A method for treating an immune-related disease in an individual in need thereof, wherein the disease is selected from the group consisting of an allergy, an inflammatory skin disease and asthma, comprising administering to the individual a therapeutically effective amount of a gingival fibroblast-derived product.

2. The method of claim 1, wherein the inflammatory skin disease is atopic dermatitis.

3. The method of claim 1, wherein the gingival fibroblast-derived product is selected from the group consisting of gingival fibroblast whole cells, a gingival fibroblast culture, a gingival fibroblast extract and a gingival fibroblast conditioned medium.

4. The method of claim 1, wherein the gingival fibroblast-derived product is obtained from gingival fibroblasts taken from the individual.

5. The method of claim 1, comprising:
taking gingival fibroblasts from the individual;
culturing the gingival fibroblasts;
obtaining a gingival fibroblast-derived product from the cultured gingival fibroblasts;
administering the gingival fibroblast-derived product to the individual.

6. The method of claim 1, wherein the gingival fibroblast-derived product is associated with at least one agent intended for the treatment of inflammatory skin disease.

7. The method of claim 1, wherein the gingival fibroblast-derived product is associated with at least one agent intended for the treatment of inflammatory skin disease selected from the group consisting of a corticosteroid, a calcineurin inhibitor, an emollient, a moisturizer.

8. The method of claim 1, wherein the gingival fibroblast-derived product is administered topically.

9. A method for treating an immune-related disease in an individual in need thereof, wherein the disease is selected from the group consisting of an allergy, an inflammatory skin disease and asthma, comprising administering to the individual a therapeutically effective amount of a composition comprising a gingival fibroblast-derived product, and comprising at least one agent intended for the treatment of an inflammatory skin disease, and comprising at least one pharmaceutically acceptable carrier or excipient.

* * * * *